United States Patent
Gaetani et al.

(10) Patent No.: US 6,846,940 B2
(45) Date of Patent: Jan. 25, 2005

(54) CERAMIDES, COMPOSITIONS THEREOF AND METHODS OF USE THEREOF

(75) Inventors: Quintino Gaetani, Clichy S/Bois (FR); Christele Guey, Deaux (FR); Eric Arbey, Aulnay sous Bois (FR); Isabelle Castiel, Jouy en Josas (FR)

(73) Assignee: L'Oreal, Paris (FR)

( * ) Notice: Subject to any disclaimer, the term of this patent is extended or adjusted under 35 U.S.C. 154(b) by 60 days.

(21) Appl. No.: 10/347,448

(22) Filed: Jan. 21, 2003

(65) Prior Publication Data

US 2004/0005282 A1 Jan. 8, 2004

Related U.S. Application Data

(60) Provisional application No. 60/352,276, filed on Jan. 30, 2002.

(30) Foreign Application Priority Data

Jan. 22, 2002 (FR) ............................................. 02 00760

(51) Int. Cl.$^7$ ............................................. C07C 233/00

(52) U.S. Cl. ............................ 554/63; 554/64; 514/613; 514/625; 514/627

(58) Field of Search ...................... 554/63, 64; 514/613, 514/625, 627

(56) References Cited

U.S. PATENT DOCUMENTS 5,869,711 A 2/1999 Philippe et al.

OTHER PUBLICATIONS

Osamu Shirota et al; "Phytosphingosines—A Facile Synthesis and Spectroscopic Protocol for Configurational Assignment"; Tetrahedron, Elsevier Science Publishers; vol. 55, No. 48; pp. 13643–13658; Nov. 26, 1999.

Gordon R. Duffin et al; Practical Syntheses of [13C]– and [14C]– labelled glucophingolipids.

*Primary Examiner*—Deborah D. Carr
(74) *Attorney, Agent, or Firm*—Oblon, Spivak, McClelland, Maier & Neustadt, P.C.

(57) ABSTRACT

Novel ceramide compounds, compositions containing them and the use of these compounds, in particular for strengthening the lipid barrier of the epidermis.

19 Claims, No Drawings

CERAMIDES, COMPOSITIONS THEREOF AND METHODS OF USE THEREOF

REFERENCE TO PRIOR FILED APPLICATIONS

This application claims priority to U.S. provisional application No. 60/352,276 filed Jan. 30, 2002, and French patent application 0200760, filed Jan. 22, 2002, both incorporated herein by reference.

SUMMARY OF THE INVENTION

The present application relates to novel ceramide compounds, particularly those of the following formula (I):

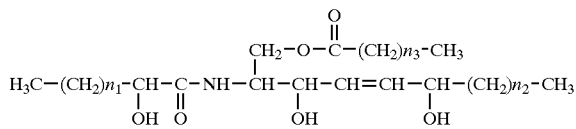

in which $n_1$ is preferably from 17 to 35, $n_2$ is preferably from 9 to 18 and $n_3$ is preferably from 12 to 18. Other subjects of the present invention include compositions comprising one or more of these compounds and the use of these compounds and compositions, in particular for strengthening the lipid barrier of the epidermis and for caring for the skin, hair and nails. Other aspects of the invention will become clear from the following description of the invention.

BACKGROUND OF THE INVENTION

The epidermis of terrestrial vertebrates has evolved such as to form an effective barrier to water loss, a factor essential to survival in a dry environment. It has been known for some decades that this barrier role is provided by a combination of lipid compounds, such as free fatty acids, cholesterol and its derivatives, and numerous ceramide compounds. The latter are extremely hydrophobic molecules, the physicochemical arrangement of which in the intercellular spaces is closely dependent on their molecular structures and on the interactions which they can exchange with proteins. Thus it is that some ceramides are bonded via covalent bonds to the proteins of the membrane of corneocytes. These bonded ceramides provide an effective bond between the other lipids and the proteins, allowing better physicochemical stability of the combination. This concept of bonded lipids (ceramides or fatty acids) is also involved in the development of skin appendages, such as the hair and nails.

The diversity and the complexity of ceramide structures are such that, despite research undertaken for some twenty years, knowledge of the subject is far from being satisfactory.

DETAILED DESCRIPTION OF THE INVENTION

The inventors have discovered novel ceramides which are effective in strengthening the barrier role of the epidermis, among other things. This strengthening makes it possible not only to achieve better protection of the skin against its drying out or the penetration of xenobiotics but indirectly, by an improvement in the functional capabilities of the skin, to combat cutaneous ageing, to limit or slow down pigmentary disorders, to retain or provide an effective immune system and thus to provide better protection against microbial or viral invasions.

The present invention relates, in a preferred embodiment, to a composition comprising, preferably in a physiologically acceptable medium, at least one ceramide and to the use of this composition in particular for strengthening the lipid barrier of the epidermis and/or for improving the quality of the epidermis. The present invention also relates to the use of these compositions in cosmetic or pharmaceutical compositions, and in particular dermatological compositions.

The inventors have also discovered novel ceramide compounds represented by the formula (I) below:

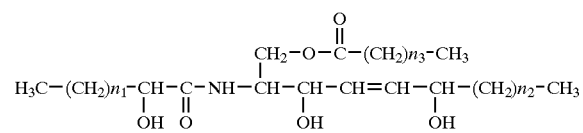

in which:
 $n_1$ is preferably from 17 to 35, more preferably from 21 to 30, preferentially from 23 to 28, more preferentially equal to 25, 26 or 27,
 $n_2$ is preferably from 9 to 18, more preferably from 11 to 15, preferentially from 11 to 13, more preferentially equal to 11, and
 $n_3$ is preferably from 12 to 18, more preferably from 14 to 16, preferentially equal to 14. These ranges include all values and subranges therebetween as if specifically written out, and of course include all endpoints.

As with all invention compounds, all enantiomers, mixtures thereof, etc., are included.

These novel ceramides may be described as being composed of a 6-OH-sphingenine base amidated by a long-chain α-hydroxylated fatty acid and esterified in the 1 position by a second saturated fatty acid with a shorter chain.

The ceramides of the present invention make it possible to strengthen the lipid barrier of the epidermis and/or to re-establish or maintain the integrity of the stratum corneum. They can therefore be employed for improving the surface appearance and the moisturizing of the skin and for protecting it, in particular protecting dry and rough skin. They can also be used as essential nutritional agents for keratinous substances (e.g., skin, hair, eyelash, nail).

Furthermore, compositions comprising at least one of these compounds can advantageously be employed to improve and/or maintain the lipid content of the human epidermis, in vivo and in vitro.

The compounds forming the subject-matter of the invention can be isolated from lipid samples taken by non-invasive methods from healthy volunteers. These lipid samples are subsequently subjected to a preparative and analytical treatment which allows the ceramide families to be separated and identified. Thus, as claimed herein, these novel ceramide compounds are different than they exist in nature in that they are in a form that is more concentrated or more pure than that found in nature. These forms are referred to herein as "substantially pure" forms.

Another potential source of the compounds of the invention lies in the use of enzymes, such as transacylases, which act on precursors or modifiers of these enzymes.

The precursors are preferably compounds of formula (II):

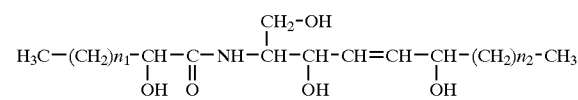

in which $n_1$ is preferably between 17 and 35, more preferably between 21 and 30, preferentially between 23 and 28, more preferentially equal to 25, 26 or 27, $n_2$ is preferably between 9 and 18, more preferably between 11 and 15, preferentially between 11 and 13, more preferentially equal to 11. These precursors correspond to the compounds of the invention not esterified in the 1 position. All these precursors having a free OH can also be used to be attached to proteins of the membrane via a strengthening ester functional group and the layer of lipid coating of the corneocytes of the skin or of its appendages.

Thus, the isolation or purification of the invention compounds, or their synthesis, is well within the ability of one of ordinary skill in the art in view of this disclosure.

A preferred embodiment of the present invention is a composition comprising, preferably in a physiologically acceptable medium, at least one ceramide compound according to the invention. This composition is advantageously a cosmetic or pharmaceutical composition, in particular a dermatological composition, comprising, preferably in a cosmetically or pharmaceutically acceptable medium, at least one compound of formula (I) according to the invention.

The composition according to the invention preferably comprises at least one compound of formula (I), alone or as a mixture, in an amount which is not limited and which can be for example from 0.005 to 20% by weight for example, more preferably from 0.01 to 10% by weight, in particular 0.05 to 5%, indeed even 0.1 to 1% by weight, with respect to the total weight of the composition. Of course, the physiologically acceptable medium in which the compounds according to the invention can be employed, and its constituents, their amount, the pharmaceutical dosage form of the composition and its method of preparation and application, can be chosen by a person skilled in the art on the basis of his or her general knowledge according to the type of composition desired in view of this disclosure.

The composition can comprise an aqueous phase which can comprise water, a floral water, such as cornflower water, a mineral water, such as water from Vittel, water from Lucas or water from La Roche-Posay, and/or a thermal water.

The aqueous phase can additionally comprise alcohols, such as $C_1$–$C_6$ monoalcohols, among which may be mentioned ethanol, propanol, butanol, isopropanol or isobutanol; and/or polyols, such as glycerol, butylene glycol, isoprene glycol, propylene glycol or polyethylene glycol.

The composition according to the invention can also comprise a fatty phase composed preferably of fatty substances which are liquid at 25° C., such as volatile or non-volatile oils of animal, vegetable, mineral or synthetic origin; of fatty substances which are solid at 25° C., such as waxes of animal, vegetable, mineral or synthetic origin; of pasty fatty substances; of gums; or of their mixtures.

The volatile oils are generally oils having a saturated vapour pressure at 25° C. at least equal to 0.5 millibar (i.e. 50 Pa).

Included among the constituents of the fatty phase are:
cyclic volatile silicones having from 3 to 8 silicon atoms and preferably from 4 to 6. They are, for example, cyclotetradimethylsiloxane, cyclopentadimethylsiloxane or cyclohexadimethylsiloxane,
cyclocopolymers of the dimethylsiloxane/methylalkylsiloxane type,
linear volatile silicones having from 2 to 9 silicon atoms. They are, for example, hexamethyldisiloxane or a PDMS of low viscosity (1 cSt). Mention may also be made of hexamethyldisiloxane and alkyltrisiloxanes, such as hexylheptamethyltrisiloxane or octylheptamethyltrisiloxane.

volatile hydrocarbonaceous oils, such as isoparaffins and in particular isododecane;
poly($C_1$–$C_{20}$)alkylsiloxanes and in particular those with end trimethylsilyl groups, among which may be mentioned linear polydimethylsiloxanes and also alkylmethylpolysiloxanes, such as cetyl dimethicone (CTFA name),
silicones modified by optionally fluorinated aliphatic and/or aromatic groups or by functional groups, such as hydroxyl, thiol and/or amine groups.
phenylated silicone oils,
oils of animal, vegetable or mineral origin and in particular animal or vegetable oils formed by esters of fatty acids and of polyols, in particular liquid triglycerides, for example sunflower, maize, soybean, cucumber, grape seed, sesame, hazelnut, apricot, almond or avocado oils; fish oils, capric/caprylic triglyceride, or vegetable or animal oils of formula $R_1COOR_2$ in which $R_1$ represents the residue of a higher fatty acid comprising from 7 to 19 carbon atoms and $R_2$ represents a branched hydrocarbonaceous chain comprising from 3 to 20 carbon atoms, for example Purcellin oil; liquid paraffin, liquid petrolatum, perhydrosqualene, or wheat germ, calophyllum, sesame, macadamia, grape seed, rapeseed, coconut, groundnut, palm, castor, jojoba, olive or cereal germ oils; fatty acid esters; alcohols; acetylglycerides; octanoates, decanoates or ricinoleates of alcohols or of polyalcohols; fatty acid triglycerides; or glycerides;
fluorinated and perfluorinated oils;
silicone gums;
waxes of animal, vegetable, mineral or synthetic origin, such as microcrystalline waxes, paraffin waxes, petrolatum wax, ozokerite or montan wax; beeswax or lanolin and its derivatives; candelilla, ouricury, carnauba or Japan waxes, cocoa butter or cork fibre or sugar cane waxes; hydrogenated oils which are solid at 25° C., ozokerites, or fatty esters and glycerides which are solid at 25° C.; polyethylene waxes and waxes obtained by Fischer-Tropsch synthesis; hydrogenated oils which are solid at 25° C.; lanolins, fatty esters which are solid at 25° C.; silicone waxes; or fluorinated waxes.

When the composition according to the invention is provided in the form of an emulsion, it can in addition optionally comprise a surfactant, preferably in an amount of 0.01 to 30% by weight with respect to the total weight of the composition. The composition according to the invention can also comprise at least one coemulsifier which can be chosen from oxyethylenated sorbitan monostearate, fatty alcohols, such as stearyl alcohol or cetyl alcohol, or esters of fatty acids and of polyols, such as glyceryl stearate.

In addition, the composition according to the invention can comprise a particulate phase which can comprise pigments and/or pearlescent agents and/or fillers commonly used in cosmetic compositions.

The pigments can be present, for example, in a proportion of 0–20% by weight with respect to the total weight of the composition and preferably in a proportion of 2–15%. They can be white or coloured, inorganic or organic, and of conventional or nanometric size. Mention may be made, among inorganic pigments and nanopigments, of titanium, zirconium or cerium dioxides, as well as zinc, iron or chromium oxides, titanium dioxide nanopigments or ferric blue. Mention may be made, among organic pigments, of carbon black, and lakes commonly employed to confer a make-up effect on the lips and skin, which lakes are calcium, barium, aluminium or zirconium salts of acid dyes, such as haloacid, azo or anthraquinone dyes.

The pearlescent agents can be present in the composition for example in a proportion of 0–20% by weight, preferably at a high level of the order of 2–15% by weight. Mention may be made, among the pearlescent agents which can be envisaged, of natural mother-of-pearl, mica covered with titanium oxide, with iron oxide, with natural pigment or with bismuth oxychloride, and coloured titanium oxide-coated mica.

The fillers, which can be present in the composition for example in a proportion of 0–20% by weight with respect to the total weight of the composition, preferably 2–10%, can be inorganic or synthetic and lamellar or non-lamellar. Mention may be made of talc, mica, silica, kaolin, nylon and polyethylene powders, Teflon, starch, boron nitride, microspheres, such as Expancel (Nobel Industrie), polytrap (Dow Corning) and silicone resin microbeads (Tospearls from Toshiba, for example).

The composition can also comprise dyes, in particular water-soluble dyes, chosen from dyes conventional in the field under consideration, such as the disodium salt of ponceau, the disodium salt of alizarin green, quinoline yellow, the trisodium salt of amaranth, the disodium salt of tartrazine, the monosodium salt of rhodamine, the disodium salt of fuchsin, or xanthophyll.

The composition according to the invention can also comprise at least one other active agent or product which can be chosen from moisturizers or humectants, such as glycerol, sorbitol, pentaerythritol or pyrrolidonecarboxylic acid and its salts; softeners; products for the treatment of skin conditions; sunscreens; germicides; preservatives; antioxidants; artificial browning agents, such as dihydroxyacetone; erythrulose, glyceraldehyde or γ-dialdehydes, such as the aldehyde derived from tartaric acid, these compounds optionally being used in combination with dyes; sunscreens, in particular water-soluble or fat-soluble sunscreens; antiperspirants, deodorants or astringents; cooling, toning, healing, keratolytic or depilatory products; scented waters; extracts from plant tissues, such as polysaccharides; anti-dandruff agents; antiseborrhoeic agents; oxidizing agents, such as bleaching agents, for example aqueous hydrogen peroxide solution; reducing agents, such as thioglycolic acid and its salts; or substances intended to improve the condition of dry or senile skin, tocopherols, vitamins E, F or A and their esters, retinoic acid, antioxidants, essential fatty acids, glycyrrhetinic acid, keratolytic agents and carotenoids.

The composition of the invention can furthermore comprise active principles which can help in preventing or in improving keratinous substances, in particular the skin and better still dry, rough and/or damaged skin, such as sphingenine, sphinganine or 4-OH-sphinganine; ceramides; glycoceramides; $C_{14-30}$ fatty acids; triglycerides; or sterols, such as cholesterol.

The composition according to the invention can comprise adjuvants such as hydrophilic or lipophilic gelling agents, hydrophilic or lipophilic additives, hydrophilic or lipophilic, in particular cosmetic or pharmaceutical, active principles, solvents, fragrances, propellants or odour absorbers. The nature and the amount of these adjuvants can be chosen by a person skilled in the art on the basis of his or her general knowledge in view of this disclosure, so as to obtain the presentation form desired for the composition. In any event, a person skilled in the art will take care to choose all the possible additional compounds and/or their amounts so that the advantageous properties of the composition according to the invention are not, or not substantially, detrimentally affected by the envisaged addition.

The compositions according to the invention can be provided in any form, including in the form of emulsions, of aqueous/alcoholic, oily or oleo-alcoholic lotions, of gels, of dispersions, of solid sticks, of sprays or of aerosol foams. For application to the skin, the composition can have the form in particular of an aqueous or oily solution; of a dispersion of the lotion or serum type; of emulsions with a liquid or semi-liquid consistency of the milk type obtained by dispersion of a fatty phase in an aqueous phase (O/W) or vice versa (W/O); of suspensions or emulsions with a soft consistency of the aqueous or anhydrous gel or cream type; of microcapsules or microparticles; or of vesicular dispersions of ionic and/or non-ionic type.

For application to the hair, the composition can preferably be in the form of aqueous, alcoholic or aqueous/alcoholic solutions; in the form of creams, gels, emulsions or foams; or in the form of aerosol compositions also comprising a pressurized propellant.

The compositions may be, for example, in the form of emollient lotions, milks or creams, milks or creams for caring for the skin or hair, make-up-removing creams, lotions or milks, foundation bases, antisun lotions, milks or creams, artificial tanning lotions, milks or creams, shaving creams or foams, aftershave lotions, shampoos or mascaras.

These compositions can also be provided in the form of lipsticks, intended either to colour the lips or to prevent chapping, or of make-up products for the eyes or of rouges and foundations for the face.

The compositions according to the invention can preferably be provided in the form:
of a product for caring for, treating or protecting keratinous substances and in particular the skin of the face or body, including the scalp, such as a care (day, night or moisturizing) composition for the face or body; an anti-wrinkle or anti-age composition for the face; a matifying composition for the face; a composition for irritated skin; a make-up-removing composition; or an optionally aftersun, in particular moisturizing, body milk;
of a sun protection, artificial tanning (self-tanning) or aftersun care composition;
of a hair composition and in particular a cream or a gel for protecting from the sun; a composition for caring for the scalp, in particular a composition for combating hair loss or for promoting hair regrowth; or an anti-parasitic shampoo;
of a product for making up keratinous substances, such as a foundation, a tinted cream, a blusher, an eyeshadow, a loose or compact powder, a concealer stick, a cover stick, a lipstick or a lipcare product; or a nail varnish, a nail care product, a mascara, a treating mascara or an eyeliner.

The compositions according to the invention find a preferred application as composition for caring for keratinous substances, in particular the skin, nails, eyelashes or hair, and especially dry and/or rough and/or damaged skin, and particularly as composition, of moisturizing type, for caring for the skin of the face and as sun protection or aftersun composition.

Another preferred embodiment of the present invention is the use of the compounds of formula (I) for the strengthening of the barrier role of the skin and for the strengthening of the keratin such as the nails and hair.

More specifically, a preferred embodiment of the invention is the use of at least one compound of formula (I) or of a composition comprising it in at least one compound of formula (I), in particular a cosmetic or pharmaceutical composition, to strengthen the lipid barrier of the epidermis, in particular of dry and/or rough and/or damaged skin, and/or to re-establish or maintain the integrity of the stratum corneum and/or to improve the surface appearance and/or the moisturizing of the skin and/or to protect the skin, in particular dry and rough skin, and/or as essential nutritional agent for keratinous substances (skin, hair, eyelash, nail) and/or to improve and/or maintain the lipid content of the human epidermis, in vivo and in vitro, and/or for the treatment of dermatological conditions reflected by an imbalance in the barrier role or in epidermal homeostasis.

The present invention also includes the use of at least one compound of formula (I) or of a composition comprising at least one compound of formula (I) in the treatment of dermatological conditions reflected by an imbalance in the barrier role or in epidermal homeostasis.

Finally, another embodiment of the invention is a process for the treatment of keratin including the skin, hair, eyelashes or nails, comprising applying a composition comprising at least one ceramide according to the invention thereto

EXAMPLES

The invention is illustrated in more detail by the following examples, but is not limited thereby Example 1

Lipid Sampling

The samplings are carried out on a cohort of 22 women (healthy volunteers) with an average age of 33.8±8.8 years and exhibiting a skin described as normal by clinicians. The samplings are carried out on the forearm using a turbine after cleaning the skin with a cotton wool swab impregnated with ether in order to remove traces of sebum. The extraction chamber of the turbine, filled with 10 ml of hexane/ethanol (2/3) mixture, is applied over a surface area of 12.56 $cm^2$. The mixture is stirred for 1 minute, is then collected using a glass syringe and is then stored in a glass receptacle at $-20°$ C.

Three samplings are thus carried out on the forearm of each person. The samples are subsequently combined, evaporated to dryness using a rotary evaporator, taken up in 1 ml of chloroform/methanol (2/1) and stored at $-20°$ C. The dry extract corresponding to these combined samplings is 36.4 mg and represents an extracted surface area of 829 $cm^2$.

Separation and Isolation of the Ceramides

In a first step, the ceramides are separated from the other categories of lipids by depositing the lipid sample obtained above on a normal phase silica cartridge (silica gel 60). After removing the neutral lipids with 10 ml of chloroform comprising 1% of acetic acid, the ceramides are eluted with 10 ml of chloroform/methanol (95/5) mixture. The ceramides are subsequently stored in 1 ml of chloroform at $-20°$ C.

In a second step, the various ceramides are separated by thin layer chromatography under the following conditions:

1.7 mg of the mixture of ceramides which are obtained on conclusion of the first stage are deposited on a 20×20 cm Whatman LK5 silica plate and 2 successive elutions are carried out with a chloroform/methanol/acetic acid mixture in the ratio 190/5/1 for the first elution and the ratio 190/9/1 for the second elution.

The classes of ceramides are located under ultraviolet (at 254 nm) after spraying a 5 mg/100 ml primulin solution over the plate. Observing in this way makes it possible to delimit 10 contiguous regions on the silica plate, numbered from 1 to 10 from the most eluted region to the least eluted region. The silica of each of these regions is scraped off, recovered and extracted several times with a chloroform/methanol (2/1) mixture. The organic phases are combined, washed with water and then evaporated to dryness to produce the pure ceramide compounds. A portion of these ceramides is subsequently redissolved in a chloroform/methanol (2/1) mixture for analytical identification.

Ceramides of the invention such that $n_1$ is between 17 and 35, $n_2$ is between 9 and 18 and $n_3$ is between 12 and 18 are recovered in spot No. 1 of the silica plate.

Structural Analysis of the Ceramide Compounds

The sample intended for analysis is divided into two fractions.

The first ceramide fraction is derivatized using benzoyl chloride. The benzoylated derivatives thus obtained are separated by high performance liquid chromatography and are injected into a mass spectrograph at the column outlet by coupled HPLC-MS.

The second fraction is subjected to alkaline hydrolysis in order to release the sphingoid bases present in the ceramides. The bases released are derivatized with ortho-phthalaldehyde before being separated by HPLC with detection by fluorescence.

The combined analytical results thus obtained make it possible to assign a specific molecular structure to each ceramide present in the sample.

A fraction A, comprising the ceramides such that $n_1$ is between 25 and 27, $n_2$ is equal to 11 and $n_3$ is equal to 14, is isolated from the mixture.

Example 2

An oil-in-water emulsion, useful for example as a skin care cream, is prepared comprising (% by weight):

| | |
|---|---|
| Glyceryl stearate | 2% |
| Sorbitan monostearate | 1% |
| Gelling agent | 0.4% |
| (Carbopol 940 ®, sold by Goodrich) | |
| Liquid fraction of karite fat | 24% |
| Fraction A of ceramides from Example 1 | 0.2% |
| Cetyl alcohol | 0.5% |
| Stearyl alcohol | 1.4% |
| Triethanolamine | 0.7% |
| Antioxidants | q.s. |
| Fragrance | q.s. |
| Preservatives | q.s. |
| Water | q.s. for 100% |

Example 3

A lipstick is prepared comprising (% by weight):

| | |
|---|---|
| Castor oil | 25% |
| Lanolin | 20% |
| Waxes | 15% |
| Fraction A of ceramides from Example 1 | 20% |
| Pigments | 8% |
| Liquid petrolatum | q.s. for 100% |

Example 4

A hair care product is prepared comprising:

| | |
|---|---|
| Decamethylcyclopentasiloxane | 25 g |
| Fraction A of ceramides from Example 1 | 0.1 g |
| Mixture of a polydimethylsiloxane hydroxylated at the chain end and of cyclomethicone (Q2-1401 from Dow Corning) | 65 g |
| Benzoate of $C_{12}$–$C_{15}$ fatty alcohols (Finsolv TN) | 4.95 g |

The above description of the invention, which includes the manner and process of making and using it, enables any person skilled in the art to make and use the same, and further puts into the hands of those of ordinary skill in this art a substantially pure compound of formula (I):

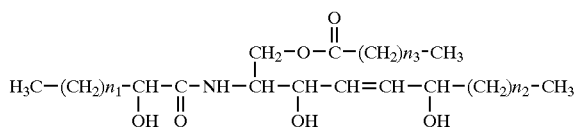

wherein $n_1$ is from 17 to 35, $n_2$ is from 9 to 18 and $n_3$ is from 12 to 18, as well as compositions comprising a physiologically acceptable medium, or a cosmetically, dermatologically or pharmaceutically acceptable medium, and at least one substantially pure compound of formula (I). Also fully described and enabled is a method for strengthening the barrier role of the skin, and/or for strengthening the nails and/or hair, and/or for re-establishing and/or maintaining the integrity of the stratum corneum, and/or for improving the surface appearance and/or the moisturizing of the skin, and/or for protecting the skin, and/or for providing nutrients to keratinous substances selected from the group consisting of skin, hair, eyelashes and, nails, and/or for improving and/or maintaining the lipid content of the human epidermis, in vivo and in vitro, comprising applying the invention composition thereto. The above description of the invention further enables the embodiments set out in the following claims, which make up a part of this disclosure.

What is claimed is:

1. A substantially pure compound having the formula (I):

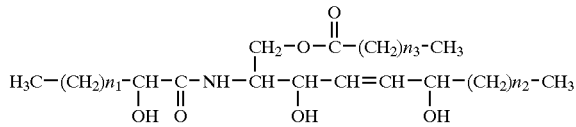

wherein $n_1$ is from 17 to 35, $n_2$ is from 9 to 18 and $n_3$ is from 12 to 18.

2. The compound according to claim 1, wherein $n_1$ is from 21 to 30.

3. The compound according to claim 1, wherein $n_2$ is from 11 to 15.

4. The compound according to claim 1, wherein $n_3$ is from 14 to 16.

5. The compound according to claim 1, wherein $n_1$ is from 21 to 30, $n_2$ is from 11 to 15, and $n_3$ is from 14 to 16.

6. A composition comprising a physiologically acceptable medium and at least one compound according to claim 1.

7. A composition according to claim 6, wherein the compound of formula (I) is present in an amount of 0.005 to 20% by weight with respect to the total weight of the composition.

8. A composition according to claim 6, further comprising at least one constituent selected from the group consisting of water, $C_1$–$C_6$ monoalcohols, polyols, volatile or non-volatile oils of animal, vegetable, mineral or synthetic origin; waxes of animal, vegetable, mineral or synthetic origin; pasty fatty substances; gums; surfactants, coemulsifiers, pigments, pearlescent agents, fillers, dyes, hydrophilic or lipophilic gelling agents, hydrophilic or lipophilic additives, active principles, solvents, fragrances, propellants, odour absorbers; moisturizers or humectants; softeners; products for the treatment of skin conditions; sunscreens; germicides; preservatives; antioxidants; artificial browning agents; sunscreens, antiperspirants, deodorants or astringents; cooling, toning, healing, keratolytic or depilatory products; scented waters; extracts from plant tissues; antidandruff agents; antiseborrhoeic agents; oxidizing agents, reducing agents; substances intended to improve the condition of dry or senile skin, tocopherols, vitamins E, F or A and their esters, retinoic acid, essential fatty acids, glycyrrhetinic acid, keratolytic agents and carotenoids; sphingenine, sphinganine or 4-OH-sphinganine; ceramides; glycoceramides; $C_{14-30}$ fatty acids; triglycerides; and sterols.

9. A composition according to claim 6, in the form of a product for caring for, treating or protecting the skin of the face or body, including the scalp, selected from the group consisting of a day, night or moisturizing composition for the face or body; an anti-wrinkle or anti-age composition for the face; a matifying composition for the face; a composition for irritated skin; a make-up-removing composition; and an optionally aftersun moisturizing body milk;

of a sun protection, artificial tanning (self-tanning) or aftersun care composition;

of a cream or a gel for protecting hair from the sun; a composition for combating hair loss or for promoting hair regrowth; or an antiparasitic shampoo; or of a foundation, a tinted cream, a blusher, an eyeshadow, a loose or compact powder, a concealer stick, a cover stick, a lipstick or a lipcare product; a nail varnish, a nail care product, a mascara, a treating mascara or an eyeliner.

10. A composition according to claim 6, in the form of a composition for caring for keratinous substances selected from the group consisting of the skin, nails, eyelashes and hair.

11. A cosmetic, dermatologic, or pharmaceutical composition comprising a cosmetically, dermatologically or pharmaceutically acceptable medium and at least one compound according to claim 1.

12. A composition according to claim 11, wherein the compound of formula (I) is present in an amount of 0.005 to 20% by weight with respect to the total weight of the composition.

13. A composition according to claim 11, further comprising at least one constituent selected from the group consisting of water, $C_1$–$C_6$ monoalcohols, polyols, volatile or non-volatile oils of animal, vegetable, mineral or synthetic origin; waxes of animal, vegetable, mineral or synthetic origin; pasty fatty substances; gums; surfactants, coemulsifiers, pigments, pearlescent agents, fillers, dyes, hydrophilic or lipophilic gelling agents, hydrophilic or lipophilic additives, active principles, solvents, fragrances, propellants, odour absorbers; moisturizers or humectants;

softeners; products for the treatment of skin conditions; sunscreens; germicides; preservatives; antioxidants; artificial browning agents; sunscreens, antiperspirants, deodorants or astringents; cooling, toning, healing, keratolytic or depilatory products; scented waters; extracts from plant tissues; antidandruff agents; antiseborrhoeic agents; oxidizing agents, reducing agents; substances intended to improve the condition of dry or senile skin, tocopherols, vitamins E, F or A and their esters, retinoic acid, essential fatty acids, glycyrrhetinic acid, keratolytic agents and carotenoids; sphingenine, sphinganine or 4-OH-sphinganine; ceramides; glycoceramides; $C_{14-30}$ fatty acids; triglycerides; and sterols.

14. A composition according to claim 11, in the form
of a product for caring for, treating or protecting the skin of the face or body, including the scalp, selected from the group consisting of a day, night or moisturizing composition for the face or body; an anti-wrinkle or anti-age composition for the face; a matifying composition for the face; a composition for irritated skin; a make-up-removing composition; and an optionally aftersun moisturizing body milk;
of a sun protection, artificial tanning (self-tanning) or aftersun care composition;
of a cream or a gel for protecting hair from the sun; a composition for combating hair loss or for promoting hair regrowth; or an antiparasitic shampoo; or
of a foundation, a tinted cream, a blusher, an eyeshadow, a loose or compact powder, a concealer stick, a cover stick, a lipstick or a lipcare product; a nail varnish, a nail care product, a mascara, a treating mascara or an eyeliner.

15. A composition according to claim 11, in the form of a composition for caring for keratinous substances selected from the group consisting of the skin, nails, eyelashes and hair.

16. A method for strengthening the barrier role of the skin, and/or for strengthening the nails and/or hair, and/or for re-establishing and/or maintaining the integrity of the stratum corneum, and/or for improving the surface appearance and/or the moisturizing of the skin, and/or for protecting the skin, and/or for providing nutrients to keratinous substances selected from the group consisting of skin, hair, eyelashes and, nails, and/or for improving and/or maintaining the lipid content of the human epidermis, in vivo and in vitro, comprising applying the composition of claim 6 thereto.

17. The method of claim 16, comprising applying said composition to dry and/or rough skin.

18. A process of treating dermatological conditions reflected by an imbalance in the barrier role or in epidermal homeostasis, comprising applying to skin the composition of claim 11, wherein said composition comprises a dermatologically acceptable medium.

19. A method for the cosmetic treatment of the skin, hair, eyelashes or nails, comprising applying to the skin, hair, nails or eyelashes a composition according to claim 11, wherein said composition comprises a cosmetically acceptable medium.

* * * * *